United States Patent [19]

Takuno

[11] Patent Number: 5,680,874

[45] Date of Patent: Oct. 28, 1997

[54] APPARATUS FOR MEASURING TOOTH MOBILITY

[76] Inventor: Tetsuo Takuno, 494-46, Kuratomi, Okayama-shi, Okayama, Japan

[21] Appl. No.: 521,185

[22] Filed: Aug. 30, 1995

[30] Foreign Application Priority Data

Sep. 26, 1994 [JP] Japan .................. 6-257601

[51] Int. Cl.$^6$ .................................................. A61B 5/103
[52] U.S. Cl. ............................................. 128/777; 128/774
[58] Field of Search .................................. 128/774, 777, 128/776, 739, 649; 3/513, 72, 215

[56] References Cited

U.S. PATENT DOCUMENTS

| | | | |
|---|---|---|---|
| 3,883,954 | 5/1975 | Simmering et al. | 128/776 |
| 3,943,913 | 3/1976 | Johnson | 128/776 |
| 4,058,115 | 11/1977 | Forster | 128/776 |
| 4,646,754 | 3/1987 | Seale | 128/649 |
| 4,881,552 | 11/1989 | Heymann | 128/774 |
| 4,904,184 | 2/1990 | Murphy et al. | 128/776 |
| 5,131,844 | 7/1992 | Marinaccio et al. | 128/776 |
| 5,518,008 | 5/1996 | Cucchiaro et al. | 128/777 |

FOREIGN PATENT DOCUMENTS

| | | | |
|---|---|---|---|
| 0427146A1 | 5/1991 | European Pat. Off. | |
| 2-062251 | 12/1990 | Japan | A61C 19/04 |

OTHER PUBLICATIONS

Automatic Diagnosis System of Tooth Mobility for Clinical Use by H. Oka, T. Yamamoto, K. Saratani and T. Kawazoe, Aug. 16, 1990, pp. 117–124.

*Primary Examiner*—Michael Buiz
*Assistant Examiner*—Patrick W. Rasche
*Attorney, Agent, or Firm*—Koda and Androlia

[57] ABSTRACT

An apparatus for measuring the teeth for looseness in a form of physical quantity of elasticity, viscosity and mass elements. The apparatus including a signal generator producing analog signals that have a desired frequency and waveform, a vibration driver for converting electrical signals supplied from the digital type oscillating signal generator into a mechanical vibration, an impedance head for detecting force and acceleration required to cause the teeth to oscillate, and an analysis device which takes in the data on the force and acceleration detected by the impedance head so as to obtain a physical quantity of the measured tooth.

5 Claims, 4 Drawing Sheets

1

APPARATUS FOR MEASURING TOOTH MOBILITY

BACKGROUND OF THE INVENTION

1. Field of the Invention

The present invention relates to a apparatus for measuring the tooth mobility with its periodontium.

2. Prior Art

Measurement of the tooth mobility or of the degree of oscillation or looseness of teeth is an examination item which is indispensable in dental therapy. This is performed for, for example, ascertaining the progression of periodontal disease, ascertaining the strength of abutment tooth for the bridge in dental prosthesis, identifying teeth which have undergone osseous ankylosis; ascertaining the completion of retention in orthodontic therapy, and ascertaining the conditions of rooting of implants.

Though measurement of the tooth mobility is thus indispensable in clinical dentistry, such measurement has been performed by sense of touch using forceps. Accordingly, considerable experience is required to make accurate measurements.

In the past, various types of apparatuses for making objective measurements of the tooth mobility have been proposed. These apparatuses can be divided into two categories: static devices and dynamic devices. The static devices apply a force to the teeth and measure slight displacements. However, these types of devices are excessively large and unsuited for everyday use. On the other hand, the dynamic devices strike the teeth or apply a vibration to the teeth, thus measuring the resulting behavior of the teeth. However, the principle of measurement is mechanically and biologically vague, and they are insufficient in terms of reliability.

Meanwhile, an apparatus for measuring the tooth mobility which attaches a somewhat clearer significance to the vague concept of "tooth mobility" has been proposed in Japanese Patent Application Publication (Kokoku) No. 2-062251 which has the Laid-Open (Kokai) No. 62-172946. This apparatus uses the measurement of mechanical impedance which is a common analysis method used in the field of vibration engineering and involves a relatively simple measurement operation.

However, this prior art apparatus uses an analog type white noise generator as the oscillating signal generator. Accordingly, because of the effect of the vibrational characteristics of an oscillation driver and other components, it is not possible to make the oscillating force constant at various different frequencies. Furthermore, with the white noise generator, it is necessary to perform a window function when a fast Fourier transform processing (hereafter referred to as "FFT processing") is performed. However, the FFT processing itself requires an additional mount of time, and a part of the weak electrical signal that is painstakingly obtained by the measuring apparatus must be discarded.

Furthermore, the above prior art discloses only that the process of the data obtained is completed when a mechanical impedance spectrum is obtained, and there is no description on how this spectrum is utilized. Such measurement results are, when examined, inconvenient and difficult to understand since they are in the form of a curve or mechanical impedance spectrum.

Moreover, recent studies unveiled that the resonance frequency of healthy teeth in the fundamental resonance mode is in the vicinity of 1 to 5 kHz. However, the measuring apparatus of the above prior art can only perform measurements at frequencies below 1 kHz. Accordingly, when this apparatus is used, resonance phenomena are not clearly observed in the region where measurement is possible.

Furthermore, in the measuring apparatus as described above, a load cell which measures contact pressure is inserted between the oscillation driver and the impedance head. This load cell has a sensor which is attached to a plate spring so as to detect strain, and the mass of the impedance head with the elasticity of the plate spring resonate at about 700 Hz. As a result, the apparatus has drawbacks which is that almost all of the signal components obtained from the impedance head are near 700 Hz, and other frequency components are inputted only to a slight extent.

SUMMARY OF THE INVENTION

Accordingly, the object of the present invention is to solve the problems in the prior art apparatuses.

Generally, teeth are standing in the alveolar bone in a "loose" state via soft tissue which is called as periodontal membrane. When an oscillation is applied to one point on the surface of a tooth, the tooth shows rotational movement mainly through deformation of the periodotal membrane. Accordingly, the movement of the tooth can be roughly approximated by means of a simple resonance model (the single-degree-of-freedom system with viscous damping) consisting of elasticity, viscosity and mass elements More specifically, as described above, teeth stand "floatingly" with a soft tissue which is called as periodontal membrane in between, and the elasticity (Yung's modulus) of a tooth and alveolar bone is about 30,000 times as hard as that of the periodontal membrane. Accordingly, when a force is applied onto one point of a tooth crown, the tooth is subject to a rotational movement around a certain point mainly through deformation of the periodontal membrane. Though the center of rotation, which is around the middle point of the root of the tooth, varies depending upon the point upon which a force is applied, the displacement of the center of rotation is minimal and therefore can be ignored.

Since the periodontal membrane, which is about 200 microns, is about 1,000 times as thick as the amplitude of vibration (which is within 0.2 microns), it can be approximated that the periodontal membrane is a complete elastic body in this condition. Furthermore, since the distance from the vibrated point to the center of rotation is more than 10 millimeters and is about 50,000 times as long as the amplitude of vibration, it is possible to approximate that the vibrated point makes a liner movement.

In other words, the behavior of the vibrated tooth can be described by the liner quadratic differential equation as shown below:

$$f = ma + cv + kx$$

wherein f is force; m, c and k are respectively severally effective mass, viscosity coefficient and elastic modulus; a, v and x are respectively severally acceleration, velocity and displacement.

In addition, substitution of cos ωt for v in the above equation makes the following equation:

$$f = A\cos(\omega t + \theta); \quad A = ((k/\omega - m\omega)^2 + c^2)^{1/2}; \quad \theta = -\tan^{-1}(k/\omega - m\omega)/c$$

where ω is angular velocity. A is called as the amplitude of mechanical impedance, and θ is the phase of it. This equation shows that each of k, c and m is measurable by different angular velocities.

The present invention is made with the recognition of the fact described above; and in the present invention, the tooth mobility is measured using physical quantities obtained for the respective elements.

The object of the present invention is accomplished by a unique structure for an apparatus for measuring the tooth mobility that includes:

a digital type oscillating signal generator which digitizes oscillation waveforms and stores the resulting digital signals in a memory and further successively performs D/A conversion on the stored digital signals so as to reproduce the signals as analog signals that have a desired frequency and waveform;

an oscillation driver which converts the electrical signals sent from the oscillating signal generator into a mechanical vibration so as to oscillate the tooth;

an impedance head which detects the force required by the oscillation driver to cause the tooth to oscillate and the acceleration involved in the oscillation; and an analysis device which puts the data detected by the impedance head in a Fourier transform processing, determines a transfer function of force relative to acceleration, and approximates the vibration of the tooth and periodontal tissue in the vicinity of the resonance point by means of a simple resonance model that consists of elasticity, viscosity and mass elements so as to obtain physical quantities for the respective elements.

With the apparatus described above, it is possible to determine the tooth mobility in terms of mechanical impedance and also in terms of various physical quantities obtained by substitution into a simple resonance model consisting of elasticity, viscosity and mass elements. Accordingly, the mechanical properties of teeth can be evaluated in the form of numerical values, and the present invention is thus exceptionally useful for research and clinical treatments in the field of dentistry.

DETAILED DESCRIPTION OF THE INVENTION

One embodiment of the present invention will be described below with reference to the accompanying drawings.

Figure 1:
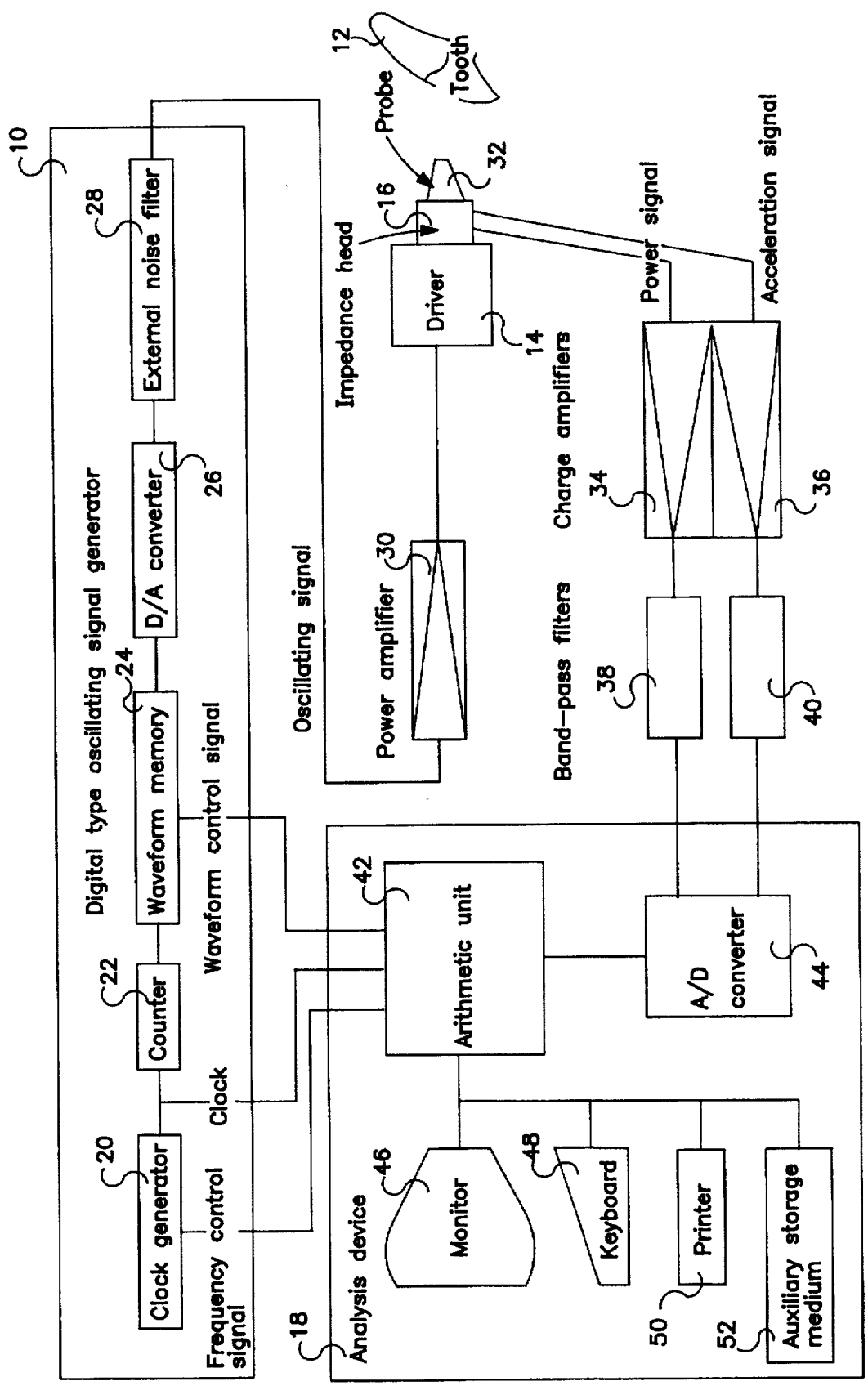
FIG. 1 is a block diagram of an apparatus for measuring the tooth mobility according to the present invention.

As seen in FIG. 1, the measuring apparatus of the present invention includes a digital type oscillating signal generator 10, a driver 14, an impedance head 16 and an analysis device 18.

The digital type oscillating signal generator 10 digitizes oscillation waveforms and stores the resulting digital signals in a memory and then successively execute D/A conversion on the stored digital signals so as to reproduce analog signals that have a desired frequency and waveform.

The driver or oscillation driver 14 causes tooth 12 to oscillate by converting the electrical signals supplied from the digital type oscillating signal generator 10 into a mechanical vibration.

The impedance head 16 detects the force required in order to cause the tooth 12 to oscillate, and it also simultaneously detects the acceleration involved in the oscillation.

The analysis device 18 takes in the data detected by the impedance head 16 and performs predetermined calculations and output.

More specifically, the digital type oscillating signal generator 10 comprises a clock generator 20 which generates digital clock pulses, a counter 22 which adds up the clock pulses, a waveform memory 24 which stores digitized oscillation waveform data and outputs data corresponding to the values indicated by the counter 22, a D/A converter 26 which converts data from the waveform memory 24 into analog signals, and an external noise filter 28 which cuts out external noise such as power supply hum, etc.

In the above, so as to afford maximum convenience for measurement, the waveform and frequency of the oscillating signal are changeable manually or by commands from the analysis device 18. In addition, the generator 10 supplies clock pulses required for the incorporation of data to the analysis device 18. The oscillating signal used in the present invention is pseudo random noise which is widely used in industrial applications. This signal is created by synthesizing sine waves of respective frequencies which are the object of analysis by the FFT processing. For example, the oscillating signal used in the present invention is obtained by superimposing 41 sine waves at 100 Hz intervals between a 1 and 5 kHz range with a fixed amplitude and random phases. Furthermore, the amplitudes of the original waveforms at each frequency are finely adjusted so that a more or less constant oscillating force is obtained at each frequency.

The output from the oscillating signal generator 10 is amplified by a power amplifier 30 and is sent to the driver 14. The driver 14 converts this signal into a mechanical vibration and causes the target tooth 12 to oscillate. The impedance head 16 is provided so as to be between the driver 14 and the tooth 12, and a probe 32 which prevents slipping of the tooth 12 during measurement is attached to the tip of the force gage of the impedance head 16.

The mass, which is, for example, 0.922 g, of the probe 32 and the tip part of the force gage (these parts will be referred to collectively as the "probe 32" hereinafter) is measured beforehand and stored in an arithmetic unit 42 of the analysis device 18 as a correction mass that is used for calculation of a correction series (described later).

The information on the force required to apply an oscillation to the tooth 12 and on the acceleration involved in the oscillation is obtained as electrical signals from the impedance head 16 in real time. The thus obtained electrical signals are amplified by respective charge amplifiers 34 and 36; afterward, frequency components not needed for measurement are cut out by band-pass filters 38 and 40, and the signals are then inputted into the analysis device 18.

The analysis device 18 includes an arithmetic unit 42, an A/D converter 44, a monitor 46, a keyboard 48, a printer 50 and an auxiliary storage medium 52.

The force signals and acceleration signals inputted into the analysis device 18 are respectively converted into digital signals by the A/D converter 44 and sent to the arithmetic unit 42. In the arithmetic unit 42, these signals are subjected to an FFT processing. The transfer function of the two values (force/acceleration) obtained by the FFT processing is determined in real time. In order to reduce measurement error, this operation is repeated a prescribed number of times so as to average the results. The function thus obtained will be referred to below as the "averaged transfer function".

Figure 2:
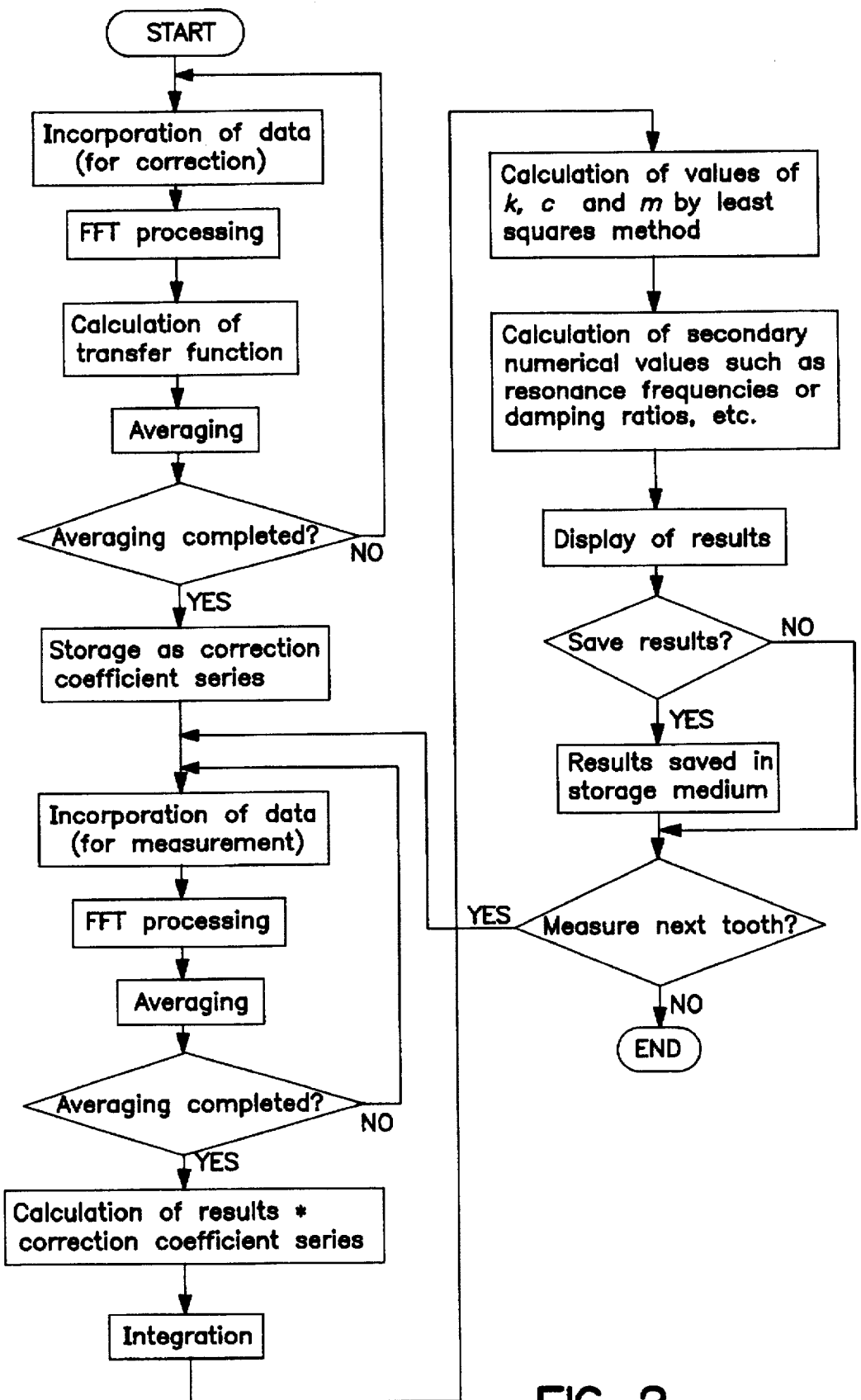
FIG. 2 is a flow chart of data processing executed in the present invention.

Next, the procedure to determine the mechanical impedance spectrum of the tooth 12 will be described. Such a procedure is described as a flow chart shown in FIG. 2.

Prior to the measurement of the tooth 12, a correction coefficient series is calculated. To do this, the driver 14 is first held in the hand with nothing in contact with the probe 32, and the averaged transfer function of the probe 32 is measured by the method described above. Theoretically, the measured function should be a constant which is independent of the frequency; however, because of slight differences in the sensitivity of the force gage and accelerometer of the impedance head 16, the function usually includes a small error. This error is treated as a sensitivity difference peculiar to the measuring apparatus and is corrected in the following manner: the averaged transfer function of the probe 32 is divided by the correction mass (0.922 g in this embodiment), a correction coefficient series is calculated using the reciprocal of the value thus obtained, and then this series is stored in the memory of the arithmetic unit 42.

Next, the probe 32 is brought so as to make contact with the tooth 12 lightly, and the averaged transfer function at this point is measured. The function thus measured is multiplied by the correction coefficient series and then integrated over frequency. The result is the mechanical impedance spectrum of the tooth and periodontal tissue. In actuality, the above integration is done by multiplication of jω wherein j is an imaginary unit and ω is an angular velocity.

A method for making an approximation from the mechanical impedance spectrum to the simple resonance model using curve fitting will be described below.

Figure 3:
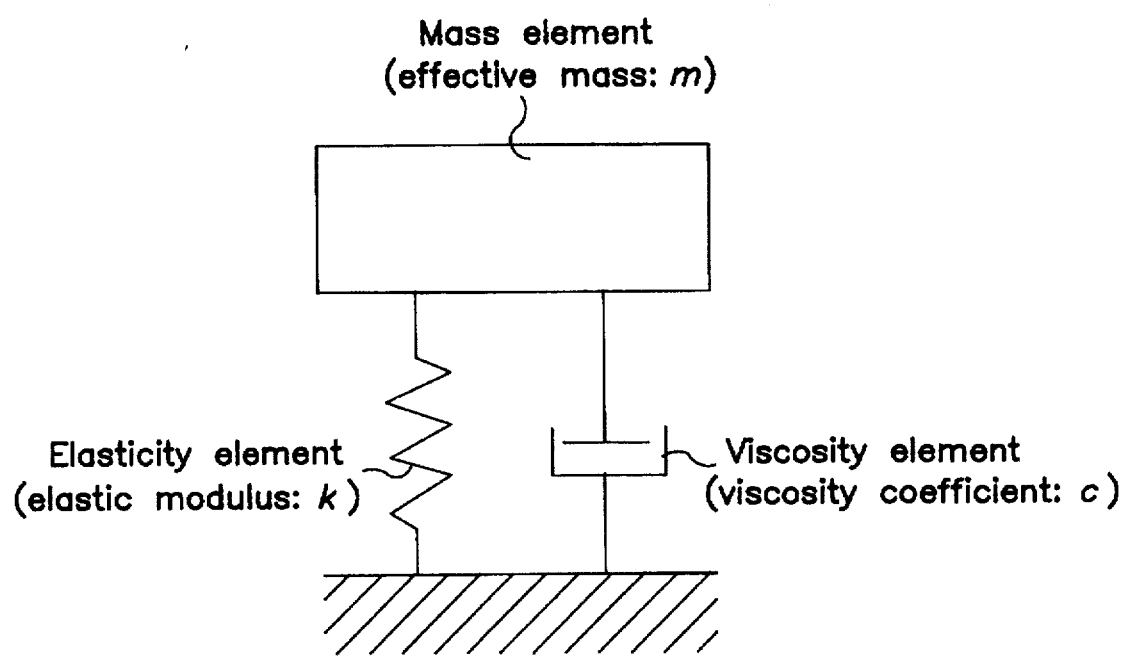
FIG. 3 is an explanatory diagram showing a simple resonance model.

As described above, teeth are in fact implanted to stand loosely in the alveolar bone via soft tissue known as the periodotal membrane; and therefore, when an oscillation is applied to one point on the surface of a tooth, the tooth shows rotational movement and liner movement mainly through deformation of the periodotal membrane. In the vicinity of the point where the oscillation is applied, these movements can be approximated as liner movement. Thus, a rough approximation can be made using the simple resonance model shown in FIG. 3.

For such an approximation, the least squares method is used. More specifically, calculations are performed using the following equations:

Elastic Modulus $k=[n\cdot\Sigma(\omega_i\cdot I_i)-\Sigma(I_i/\omega_i)\cdot\Sigma\omega_i^2]/[\Sigma\omega_i^{-2}\cdot\Sigma\omega_i^2-n^2]$ Viscosity Coefficient $c=\Sigma R_i/n$ Effective Mass $m=[n\cdot k+\Sigma(\omega_i\cdot I_i)]/\Sigma\omega_i^2$ In the above, n: Number of data $\omega_i$: Angular velocity of the i-th datum $R_i$: Real component of the i-th mechanical impedance datum $I_i$: Imaginary component of the i-th mechanical impedance datum With the above equations, the respective physical quantities of the elasticity, viscosity and mass elements are determined as the elastic modulus k, viscosity coefficient c, and effective mass m; and these physical quantities and the mechanical impedance spectrum are displayed on the monitor 46 and printed out by printer 50 as well as saved on an auxiliary storage medium 52. Needless to say, the saved datum can be completely retrieved in the form of the original.

Figure 4:
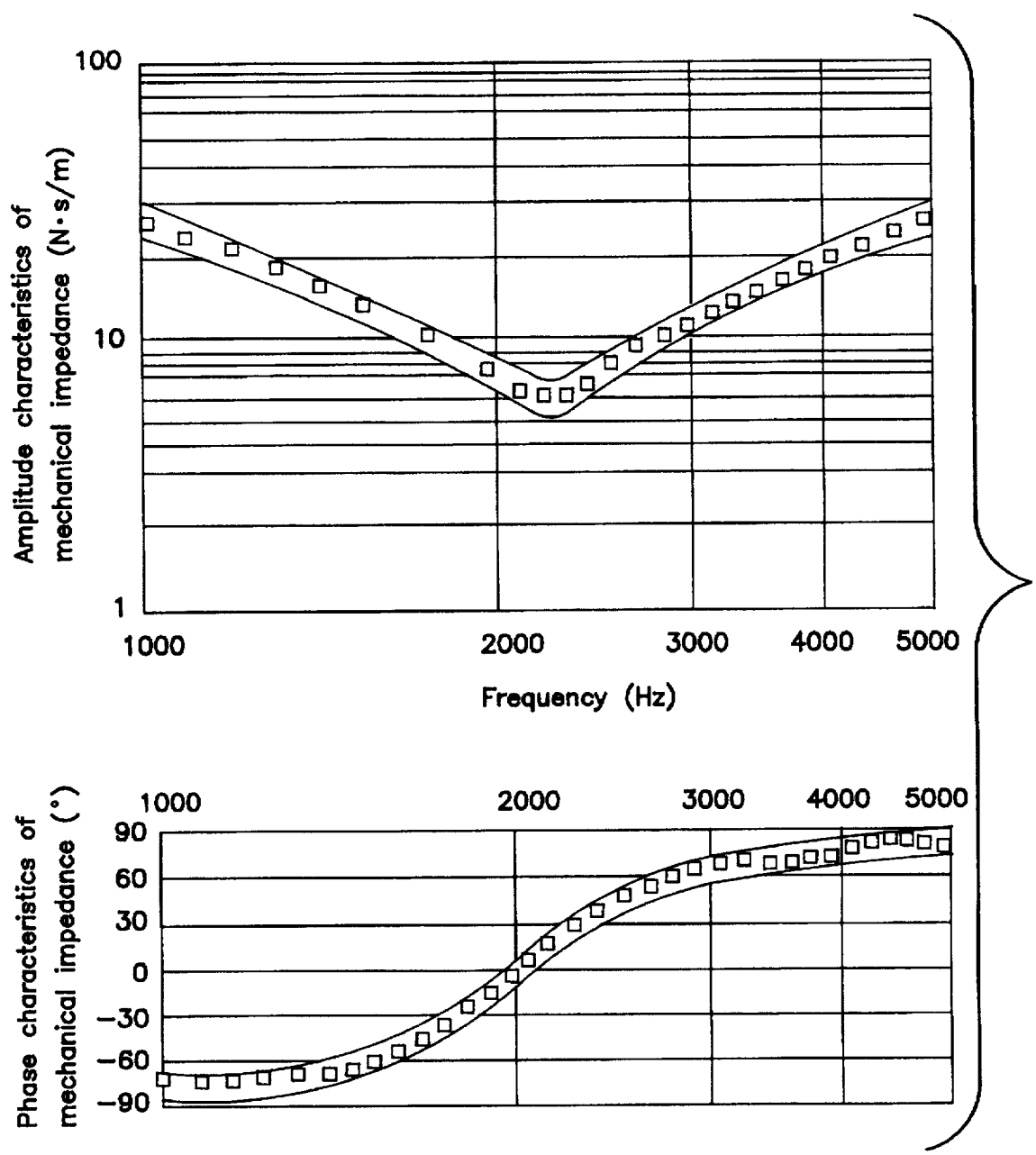
FIG. 4 shows characteristic curves of measurement results obtained by the present invention.

FIG. 4 shows a print-out of an example of measurement of the lower incisors measured by the measuring apparatus of the present invention and the analysis results. The same is displayed on the monitor 46.

In the upper graph, the amplitude characteristics of the measured mechanical impedance spectrum are plotted by filled squares; while in the lower graph, the phase characteristics are likewise plotted. Theoretical curves calculated on the basis of values of k, c and m determined from these data by curve fitting are shown as thick lines. The squares and the theoretical curves show close agreement, which means that curve firing was appropriately performed.

The individual information for the patient is shown above the graphs along with the measurement positions and analysis results, etc. Values such as resonance frequencies, damping ratios, etc., which are secondarily calculated from the values of k, c and m, may be indicated along with the k, c and m in the present embodiment.

The analysis results obtained for the teeth used in this measurement example show more or less average values, and no particularly abnormal findings are observed.

If numerous healthy teeth are measured according to tooth type using the measuring apparatus of the present invention and mean values and standard deviations are determined accordingly, a statistical evaluation can be obtained which may be used to determine whether or not the measurement results obtained for a given tooth are within normal ranges. Furthermore, by measuring only the teeth of a particular disorder, it may be possible to discover peculiar patterns for that disorder by comparing the results of measurement of the disorder with the results obtained for healthy teeth.

As seen from the above, according to the present invention, evaluations are made on the vibrational characteristics of teeth using respective physical quantities obtained for elasticity, viscosity and mass elements. In addition, in such evaluations, the quantities may be observed individually, or may be summarized in terms of values such as resonance frequencies, damping ratios, etc. Thus, it is possible to evaluate the tooth mobility objectively, rationally and conveniently from a broad range of standpoints.

I claim:

1. An apparatus for measuring a tooth mobility comprising:

a digital type oscillating signal generator means for digitizing oscillation waveforms and storing resulting digital signals in a memory, said generator means further for successively executing digital to analog D/A conversion on said stored digital signals for reproducing said signals in a form of analog signals that have a desired frequency and waveform;

a driver means for causing the tooth to oscillate by converting electrical signals of the oscillating signal generator into a mechanical vibration;

an impedance head means for detecting a force required by said driver means to cause said tooth to oscillate and an acceleration involved in said oscillation; and an analysis means for executing a Fourier transform processing on said force and acceleration detected by said impedance head means, determining a transfer function of said force relative to said acceleration, approximating a vibration of said tooth and periodontal tissue in a vicinity of a resonance point as a simple resonance model that consists of elasticity, viscosity and mass elements and calculating a quantity of each of said elasticity, viscosity and mass elements by a least squares method.

2. An apparatus for measuring a tooth mobility according to claim 1, wherein secondary numerical values used in vibration engineering comprising resonance frequencies and damping ratios are obtained from said quantity of each of said elasticity, viscosity and mass elements.

3. An apparatus for measuring tooth mobility according to claim 1, wherein a frequency of said oscillation waveforms is from 1 to 5 kHz.

4. An apparatus for measuring oscillation of a tooth comprising:

a digital type oscillating signal generator means for digitizing oscillation waveforms, storing resulting digital signals in a memory and performing distal to analog D/A conversion on said digital signals so as to reproduce said signals in a form of analog signals of a desired frequency and waveform;

a driver means connected to said oscillating signal generator means, said driver means for converting said digital signals sent from said oscillating signal generator means into a mechanical vibration so as to oscillate the tooth via a probe;

an impedance head means mounted on said driver means, said impedance head means for detecting a force and acceleration required for causing said tooth to oscillate; and an analysis means for executing a Fourier transform processing on said force and acceleration detected by said impedance head, determining a transfer function of said force relative to said acceleration, approximating a vibration of said tooth and periodontal tissue in a vicinity of a resonance point as a simple resonance model that consists of elasticity, viscosity and mass elements and calculating a quantity of each of said elasticity, viscosity and mass elements by a least squares method.

5. An apparatus for measuring oscillation of a tooth according to claim 4, wherein a frequency of said oscillation waveforms is from 1 to 5 kHz.

* * * * *